US011162833B2

(12) United States Patent
Buess

(10) Patent No.: US 11,162,833 B2
(45) Date of Patent: Nov. 2, 2021

(54) METHOD FOR VERIFYING A CALIBRATION OF A SPIROMETER

(71) Applicant: ndd Medizintechnik AG, Zurich (CH)

(72) Inventor: Christian Buess, Horgen (CH)

(73) Assignee: ndd Medizintechnik AG, Zurich (CH)

( * ) Notice: Subject to any disclaimer, the term of this patent is extended or adjusted under 35 U.S.C. 154(b) by 268 days.

(21) Appl. No.: 16/404,155

(22) Filed: May 6, 2019

(65) Prior Publication Data
US 2019/0339108 A1    Nov. 7, 2019

(30) Foreign Application Priority Data

May 7, 2018    (EP) ..................................... 18170990

(51) Int. Cl.
*G01F 25/00*      (2006.01)
*A61B 5/087*      (2006.01)
*G01F 1/66*       (2006.01)

(52) U.S. Cl.
CPC .......... *G01F 25/0053* (2013.01); *A61B 5/087* (2013.01); *G01F 1/667* (2013.01)

(58) Field of Classification Search
CPC ..... G01F 25/0053; G01F 1/667; A61B 5/087; A61B 2560/0223; A61B 5/091; A61B 8/00
See application file for complete search history.

(56) References Cited

U.S. PATENT DOCUMENTS

| | | | |
|---|---|---|---|
| 5,419,326 A * | 5/1995 | Harnoncourt | A61B 5/087 600/438 |
| 5,748,504 A | 5/1998 | Fletcher-Haynes | |
| 7,152,490 B1 | 12/2006 | Freund, Jr. et al. | |
| 2008/0208056 A1 | 8/2008 | Kuhn et al. | |
| 2010/0095782 A1 | 4/2010 | Ferencz et al. | |
| 2016/0128608 A1 | 5/2016 | Buess et al. | |

FOREIGN PATENT DOCUMENTS

| | | |
|---|---|---|
| EP | 3017760 A1 | 5/2016 |
| EP | 3403578 A1 | 11/2018 |
| EP | 3403813 A1 | 11/2018 |

OTHER PUBLICATIONS

Gwen S Skloot, Nicole T Edwards, Paul L Enright, "Four-Year Calibration Stability of the EasyOne Portable Spirometer", Published by Respiratory Care, Jul. 2020, vol. 55, No. 7 (Year: 2010).*
V.C. Moore, "Spirometry: step by step", Published by Breathe, Mar. 2012, vol. 8, No. 3 (Year: 2012).*
Maria McNeill, Geraldine Nolan, "Spirometry: Performance and Interpretation for Healthcare Professionals", Published by the Faculty of Respiratory Physiology, Version 1, Apr. 2015 (Year: 2015).*
Miller, M. et al., "Standardisation of spirometry," The European Respiratory Journal, vol. 26, No. 2, Aug. 2005, 20 pages.

* cited by examiner

Primary Examiner — Herbert K Roberts
Assistant Examiner — John M Royston
(74) Attorney, Agent, or Firm — McCoy Russell LLP

(57) ABSTRACT

The invention relates to a method for verifying a calibration of an ultrasonic spirometer, the method comprising determining an actual value of a distance between a first ultrasonic transducer and a second ultrasonic transducer of a spirometer, determining a difference between the actual value of the distance and a nominal value of the distance that is assigned to the spirometer, and accepting an actual calibration of the spirometer if an absolute value of the difference is smaller than or equal to a first threshold value, or refusing the actual calibration of the spirometer if the absolute value of the difference is bigger than the first threshold value, wherein the first threshold value is 5% of the nominal value of the distance. The invention further relates to a spirometer that is adapted to carry out this method as well as to a method for calibrating a spirometer.

19 Claims, No Drawings

METHOD FOR VERIFYING A CALIBRATION OF A SPIROMETER

CROSS REFERENCE TO RELATED APPLICATIONS

The present application claims priority to European Application No. 18 170 990.8 entitled "METHOD FOR VERIFYING A CALIBRATION OF A SPIROMETER," filed May 7, 2018. The entire contents of the above-listed application are hereby incorporated by reference for all purposes.

TECHNICAL FIELD

The present application relates to a spirometer as well as methods for calibrating a spirometer and verifying a calibration of a spirometer.

DESCRIPTION

Ultrasonic spirometers are devices for measuring the mean velocity of a flowing gas along an ultrasonic transmission path. Based on this velocity, the flow rate of the flowing gas is determined. If the time is additionally measured, the volume of inspired and exhaled breathing gas (such as breathing air) of a patient can be determined. The analysis of this data can be used to obtain analytic or diagnostic information on the lung of the patient and on the gas exchange within the lung of the patient.

An ultrasonic spirometer typically comprises two ultrasonic transducers that are mounted into a housing of the spirometer. These ultrasonic transducers are typically mounted in a cushioned way to avoid structure-borne noise. Structure-borne noise is noise that is transmitted from a first ultrasonic transducer to a second ultrasonic transducer via the housing (or other structural parts) of the spirometer, i.e. not via the flowing gas. Structure-borne noise can lead to incorrect measurements.

Since there are always small variations in the exact position of the ultrasonic transducers, a spirometer needs to be calibrated prior to its intended use. According to techniques known from prior art, an exactly defined volume of gas is guided through the spirometer. By measuring the flow rate and the time needed for the exactly defined volume of the gas to pass the spirometer, the volume of the gas is measured. The calibration is carried out by defining and adjusting a factor that serves to bring the value of the factually measured gas volume in congruence with the exactly known gas volume guided through the spirometer.

The ATS/ERS guidelines for spirometry (M. R. Miller et al. Standardisation of Spirometry. *European Respiratory Journal,* 2005, 26: 319-338) require that the calibration of the spirometer is checked at least once a day. This requires again guiding an exact volume of gas through the spirometer. Typically, a 3-liter pump (providing exactly 3 liters of gas) is used for calibrating and re-calibrating a spirometer. Such a pump is also referred to as calibration pump and is calibrated itself in order to ensure that it provides exactly 3 liters of gas.

However, this calibration with a calibration pump leads to inaccuracies for several reasons. The main factors for such inaccuracies are: a wrong connection between the calibration pump and the spirometer, defects in fluid tightness of the pump itself (also dynamic defects in fluid tightness that are dependent on the pumping speed), and wrong execution of the calibration by a user (too high or too low pumping speed or incomplete pump stroke). Thus, calibrating a spirometer is a laborious process connected to a number of sources of inaccuracies.

It is an object of the present invention to provide methods for calibrating, recalibrating and verifying the calibration of a spirometer that can be easier applied than the calibration methods known from prior art.

This object is achieved by a method for verifying a calibration of an ultrasonic spirometer. This method comprises the steps explained in the following. Thereby, the term "spirometer" is used for "ultrasonic spirometer" in the following. In a first step, an actual value of the distance between a first ultrasonic transducer and a second ultrasonic transducer of the spirometer is determined. Afterwards, a difference between the actual value of the distance and a nominal value of the distance is calculated. Thereby, the nominal value of the distance has been previously assigned to the spirometer. An absolute value of this difference is then used to determine whether or not an actual calibration of the spirometer is to be considered still valid. To be more precisely, the actual calibration of the spirometer is accepted as still correct if an absolute value of the difference is smaller or equal to a first threshold value. Contrary, the actual calibration of the spirometer is refused if the absolute value of the difference is bigger than the first threshold value. It turned out that a sufficiently high accuracy can be obtained if the first threshold value corresponds to 5% of the nominal value of the distance.

This novel method for verifying a calibration of a spirometer does not necessitate any calibration pump any longer. Rather, it can be carried out in a fully automatically way guaranteeing an information on whether or not an original calibration of the spirometer is still valid. This verification of calibration can be carried out at any time by request of the user or, e.g., automatically in predefined time intervals such as once a day, twice a week, once a week, twice a month or once a month. Since this automated process does no longer depend on the technical abilities of the user or the quality of a calibration pump, the presently claimed method is much more reliable than the methods known from prior art. The probability of an incorrect calibration of the spirometer is significantly reduced with respect to the methods known from prior art making use of a calibration pump.

The method is particularly useful if the ultrasonic transducers have been precisely mounted into the spirometer housing. In an embodiment, the method is applied on spirometers in which the distance between the first ultrasonic transducer at the second ultrasonic transducer is known with an accuracy of ±0.2 mm. The total distance between the first ultrasonic transducer second ultrasonic transducer is typically around 50 mm. A distance tolerance of ±0.2 mm results in variations of the gas flow calibration of approximately ±0.4%.

In an embodiment, the first threshold value is 4.5%, in particular 4.0%, in particular 3.5%, in particular 3.0%, in particular 2.5%, in particular 2.0%, in particular 1.5%, in particular 1.0%, in particular 0.5% of the nominal value of the distance. The lower the threshold value, the better the actual value of the distance needs to correspond to the nominal value of the distance in order to pass the verification process.

If the verification of calibration results in refusing a current calibration, this is a clear indication that the spirometer shows a malfunction and needs to be serviced. Optionally, no further measurements will be possible with the respective spirometer until the verification of calibrations will have been passed again successfully.

The calculated distance between the first ultrasonic transducer and the second ultrasonic transducer is used in the following formula (1) to determine the flow rate of a gas flowing through the spirometer:

$$F = a \cdot \frac{L}{2\cos\alpha} \cdot \frac{t_1 - t_2}{t_1 \cdot t_2} \qquad (1)$$

Thereby, F is the average flow rate of the gas flowing through the spirometer within a region of an ultrasound transmission line between the first ultrasonic transducer and the second ultrasonic transducer, a is a factor considering geometric parameters like the dimension of the ultrasonic path and being dependent on the velocity of the flowing gas, L is the distance between the first ultrasonic transducer and the second ultrasonic transducer as determined during calibration and verified during verification of calibration, $\alpha$ is the angle between the gas flow direction and the ultrasonic path, $t_1$ is the transit time of an ultrasonic pulse from the first ultrasonic transducer to the second ultrasonic transducer, and $t_2$ is the transit time of an ultrasonic pulse from the second ultrasonic transducer to the first ultrasonic transducer.

The factor a can differ about 10 to 40%, in particular about 20 to 30%, between low and high velocities of the flowing gas. Thus, it is a function of the flow velocity. Typically, it is empirically determined for a specific setup of a spirometer.

If the gas is flowing, the transit times $t_1$ and $t_2$ are different since an ultrasonic pulse is faster in downstream direction (with the gas flow) than in upstream direction (against the gas flow).

In an embodiment of the verification method, the actual value of the distance between the first ultrasonic transducer and the second ultrasonic transducer is determined by an ultrasonic measurement. This measurement is performed while there is gas present between the first ultrasonic transducer and the second ultrasonic transducer, wherein the gas does not flow, i.e., it has a flow rate of zero. In such a case, a transit time $t_1$ of an ultrasonic pulse from the first ultrasonic transducer to the second ultrasonic transducer is—under ideal conditions—exactly as long as a transit time $t_2$ of an ultrasonic pulse from the second ultrasonic transducer to the first ultrasonic transducer. Under real conditions, often small deviations between $t_1$ and $t_2$ can still be measured even in case of an apparently non-flowing gas. The length is determined using the following equation (2):

$$L = t_{1,2} \cdot c = t_{1,2} \cdot \sqrt{\frac{\kappa RT}{M}} \qquad (2)$$

Thereby, L is the distance between the first ultrasonic transducer and the second ultrasonic transducer, $t_{1,2}$ is a transit time of an ultrasonic pulse calculated from a transit time of an ultrasonic pulse from the first ultrasonic transducer to the second ultrasonic transducer, or a transit time of an ultrasonic pulse calculated from a transit time of an ultrasonic pulse from the second ultrasonic transducer to the first ultrasonic transducer, or a mean (an average) transit time of an ultrasonic pulse calculated from a transit time of an ultrasonic pulse from the first ultrasonic transducer to the second ultrasonic transducer and a transit time of an ultrasonic pulse from the second ultrasonic transducer to the first ultrasonic transducer, $\kappa$ is the quotient between the specific heat capacity of gas at constant pressure $c_P$ and the specific heat capacity of the gas at constant volume $c_V$, i.e., $c_P/c_V$, R is the universal gas constant (ca. 8.314 J/(mol·K)), T is the absolute temperature of the gas (indicated in K), and M is the molar mass of the gas.

In an embodiment, the transit time from the first ultrasonic transducer to the second ultrasonic transducer and the transit time from the second ultrasonic transducer to the first ultrasonic transducer are in fact equally long. This is typically true if there is no flow and if there are no measuring errors (or only measuring errors that can be considered to be negligible).

In an embodiment, the transit time $t_{1,2}$ is calculated from the measured transit time(s) by subtracting an offset, which is—at least in theory—identical for both transmission paths. This offset takes two parameters into account, namely a transit time of the ultrasonic pulse within an impedance matching layer and a time delay in detecting an ultrasonic pulse that is inherent to the measuring technique.

To be more precisely, a transducer comprises a piezo transducer and an impedance matching layer applied to the piezo transducer. The transit time of an ultrasonic pulse in a defined distance in air differs from the transit time of the ultrasonic pulse in the same distance in the impedance matching layer. Typically, the thickness of the impedance matching layer is well known so that a transit time difference with respect to air can be easily calculated for a specific impedance matching layer.

Furthermore, there is a difference between a theoretic arrival time of an ultrasonic pulse and a detected arrival time due to the oscillating build-up behavior of the transducer. Expressed in other words, it needs some time to detect an ultrasonic pulse after it has reached the transducer; there is a time delay in detecting the ultrasonic pulse.

In an embodiment, the first ultrasonic transducer and/or the second ultrasonic transducer is an ultrasonic transmitter, an ultrasonic receiver or an ultrasonic transceiver. If one of the first and second ultrasonic transducers is an ultrasonic transmitter, the respective other one is an ultrasonic receiver.

In an embodiment, the gas is a gas mixture of different gas mixture components, wherein the molar mall of the gas mixture is calculated according to the following equation (3):

$$M = \sum_{i=1}^{n} f_i \cdot M_i \qquad (3)$$

Thereby, $f_i$ is the fraction of a gas mixture component i in the gas mixture, $M_i$ is the molar mass of the gas mixture component i in the gas mixture, and n is the number of gas mixture components in the gas mixture.

In an embodiment, the gas is not a pure gas of a single element, but rather a gas mixture comprising different gas mixture components (each gas mixture component being itself a gas). Thereby, an estimated composition of the gas mixture is used to calculate its molar mass. In doing so, it is not necessary to exactly determine the composition of the gas mixture. Rather, gas mixture components having a low abundance (such as trace gases) are simply ignored. Then, an appropriate gas mixture composition is assumed that corresponds to a mean expected composition of the gas mixture.

In an embodiment, the gas mixture is (ambient) air. To facilitate the calculation of the molar mass of the air, an estimated composition of 72-84 vol.-% nitrogen, 15-25 vol.-% oxygen, 0.5-1.5 vol.-% argon, 0.01-1.5 vol.-% carbon dioxide, and 0-10 vol.-% water vapor is assumed. The percentages of the individual gas mixture components (i.e., nitrogen, oxygen, argon, carbon dioxide, and optionally water) are chosen such that they sum up to 100%. Further components being present in ambient air in traces need not to be considered. Their presence or absence does not significantly influence the molar mass of air so that it does not disturb the accuracy of the present method if these trace gases are not considered. By such an approach, a molar mass of air lying in a range of approximately 25 to 34 g/mol, in particular of approximately 26 to 33 g/mol, in particular of approximately 27 to 31 g/mol, in particular of approximately 28 to 30 g/mol results. Using a molar mass out of such a molar mass range results in sufficiently precise results.

In an embodiment, the absolute temperature of the gas is not directly measured. Rather, the absolute temperature of the flow tube holder of the spirometer is measured and is deemed to be the absolute temperature of the gas. The flow tube holder is a part of the spirometer that serves for housing the flow tube (also often referred to as breathing tube). An appropriate flow tube holder is disclosed in European patent application 17 171 303.5 1 assigned to the present applicant. Temperature deviations of up to 0.5 K, in particular up to 0.4 K, in particular up to 0.3 K, in particular up to 0.2 K, in particular up to 0.1 K (corresponding to typical measuring errors of thermometers) are considered to be negligible. Typically, a temperature equilibration between a non-flowing gas in the spirometer and the surrounding spirometer is effected in a few seconds (such as 1 to 10 seconds, in particular 2 to 9 seconds, in particular 3 to 8 seconds, in particular 4 to 7 seconds, in particular 5 to 6 seconds). Therewith, it is not necessary to perform a technically demanding temperature measurement of the gas in the spirometer, but rather to rely on the temperature of the flow tube holder of the spirometer, i.e. to measure the temperature of a solid body.

In an embodiment, the distance is normalized to an arbitrary standard temperature. In doing so, one can account for distance variations due to thermal expansion of the material. The normalization can, e.g., by performed by dividing the calculated distance by the measured absolute temperature and by multiplying it afterwards with an arbitrary standard temperature, such as room temperature. Then, the distance is indicated as distance at a specific temperature, namely, at the chosen standard temperature.

In an embodiment, the verification of calibration is performed when the flow tube is inserted into a flow tube holder of the spirometer. In such a case, the verification is carried out in a very similar manner like the actual flow measurements performed afterwards. If the flow tube is inserted into the flow tube holder of the spirometer during the verification process, it needs to be inserted therein during the original calibration process, too.

To increase the overall accuracy of the present method, it is advisable to use flow tubes that have been manufactured very precisely. In particular, such flow tubes should have a high dimensional accuracy in order to serve for a highly reliable and reproducible cross section of the flow tube that defines the distance to be covered by the ultrasonic waves along the sound transmission path through the gas flow. Therefore, in an embodiment, flow tubes having openings covered by a mesh that is smoothened or straightened during the manufacturing process of the flow tubes are used. Appropriate flow tubes are, e.g., disclosed in European patent application 17 171 300.1 assigned to the present applicant. Furthermore, the reliability of the present method can be enhanced if the inserted flow tubes are present in a defined position in the spirometer. Therefore, in an embodiment, the position of the flow tube within the flow tube holder is checked to take care that the flow tube is correctly positioned. Appropriate flow tubes, the position of which can be easily checked in the spirometer, are described in European patent application EP 3 017 760 A1 assigned to the present applicant.

It turned out that structure-borne noise of a spirometer can impair a flow rate measurement and also the calibration of a spirometer. To avoid such undesired effects, structure-borne noise of the spirometer is additionally determined in an embodiment. Then, the actual calibration of the spirometer is only accepted if an absolute value of the distance difference is smaller than or equal to the first threshold value (as explained above) and if additionally, the amount of structure-borne noise is smaller than or equal to a second threshold value. Thus, the actual calibration is only accepted, if those two conditions are met concurrently. If, on the other hand, the amount of structure-borne noise is bigger than the second threshold value, the calibration is refused, regardless of whether or not the absolute value of the distance between the first ultrasonic transducer and the second ultrasonic transducer is smaller or bigger than the first threshold value. Thus, sufficiently low structure-borne noise is, in this embodiment, the necessary requirement to pass the verification of calibration. If the structure-borne noise is too high, this is a clear indication that the spirometer is defect. E.g., the soft cushioning of the ultrasonic transducers might have become stiff. Or, e.g., a structure-borne noise bridge might have been formed within the spirometer. At the same time, the distance between the ultrasonic transducers might still be within the required range.

In an embodiment, the second threshold value lies in a range of 0.5 to 5.0% of the primary received ultrasonic signal. In an embodiment, the second threshold value is 5.0%, in particular 4.5%, in particular 4.0%, in particular 3.5%, in particular 3.0%, in particular 2.5%, in particular 2.0%, in particular 1.5%, in particular 1.0%, in particular 0.5% of the primary received ultrasonic signal. The lower the threshold value, the lower the actual value of the detected structure-borne noise needs to be in order to fulfil this test criterion.

In an embodiment, the amount of structure-borne noise is determined prior to determining the distance between the first ultrasonic transducer and the second ultrasonic transducer. To be more precisely, the structure-borne noise is determined by measuring the amplitude of the first ultrasonic transducer and/or the second ultrasonic transducer in a time window, wherein this time window lies before the time window in which the transit time of an ultrasonic pulse from the first ultrasonic transducer to the second ultrasonic transducer or vice versa is measured. This determination of the structure-borne noise can be carried out by means of special electronics implemented in a control device for the spirometer or in the spirometer itself.

In an embodiment, the amount of structure-borne noise is determined while there is gas present between the first ultrasonic transducer and the second ultrasonic transducer that is not flowing. Thus, in this embodiment, the amount of structure-borne noise is generally determined with the same settings of the spirometer like the distance between the first ultrasonic transducer and the second ultrasonic transducer.

In an embodiment, the amount of structure-borne noise is determined during the proper gas flow measurement, i.e., while gas is flowing through the flow tube of the spirometer.

In an aspect, the present invention also relates to a method for verifying a calibration of a spirometer, wherein this method does not make use of determining an actual value of the distance between the first ultrasonic transducer and the second ultrasonic transducer, but solely relies on verifying the calibration of the spirometer by detecting the structure-borne noise and by deciding only upon the detected structure-borne noise whether or not an actual calibration of the spirometer needs to be refused. This method can also be described in the following way:

Method for verifying a calibration of a spirometer, the method comprising the following steps: a) determining an amount of structure-borne noise of the spirometer; and b) refusing an actual calibration of the spirometer if the amount of structure-borne noise is bigger than a second threshold value.

All embodiments explained with respect to the embodiments of the previously explained methods—in particular the embodiments relating to the determination of structure-borne noise—can also be applied to this independently disclosed and claimed method for verifying the calibration of a spirometer on the basis of structure-borne noise only.

In an aspect, the present invention relates to a spirometer that is suited to carry out a method according to the preceding explanations. Such a spirometer has first ultrasonic transducer and the second ultrasonic transducer. Furthermore, it comprises a control unit that is specifically adapted and arranged to automatically carry out a method according to the preceding explanations. Thereby, the method can be carried out in predetermined intervals (such as time intervals or after a predetermined number of spirometric analyses performed by the spirometer) or by request of a user. Regarding the details of the performed method, reference is made to the explanations given above.

In an embodiment, the spirometer comprises an electronic memory that serves for storing the nominal value of the distance between the first ultrasonic transducer and the second ultrasonic transducer. Then, it is particularly simple for the control unit to perform the comparison between the nominal value and the actual value of the distance between the first ultrasonic transducer and the second ultrasonic transducer.

In an aspect, the present invention also relates to a method for (initially) calibrating a spirometer, wherein the method comprises the steps explained in the following. In a first step, an actual value of a distance between a first ultrasonic transducer and a second ultrasonic transducer of a spirometer is measured or is considered to be known on the basis of a measured distance value of an identically constructed spirometer (e.g., of a spirometer of the same manufacturing batch of spirometers, wherein care is taken that the manufacturing tolerances are kept at a (very) low level). This actual value is then taken as nominal value of the distance between both ultrasonic transducers. This nominal value is then assigned to the spirometer. After this initial calibration, which is typically performed during manufacturing of the spirometer, a verification of this calibration can be carried out at any time later on. Thus, it is no longer necessary to use a calibration pump for calibration purposes. Furthermore, no manual production steps works are any longer necessary for calibrating the spirometer. This significantly facilitates the production process of the spirometer and reduces production costs.

In an embodiment, the nominal value is mechanically measured with an appropriate measuring device, such as calipers. If the depth of the ultrasonic transducers is known, the distance between the rear side of the first ultrasonic transducer and the rear side of the second ultrasonic transducer can be measured. By subtracting twice the depth of a single ultrasonic transducer, the distance between the front sides of the ultrasonic transducers results. This distance corresponds to the distance to be covered by the ultrasonic waves on their way from the first ultrasonic transducer to the second ultrasonic transducer.

In an embodiment, the nominal value of the distance is determined in the same way as the actual value of the distance as explained above. To be more precisely, the nominal value is determined while there is gas present between the first ultrasonic transducer and the second ultrasonic transducer, wherein the gas is not flowing. Then, once again the following equation (2) can be used for calculating the distance based on the measured transit time of an ultrasonic pulse from the first ultrasonic transducer to the second ultrasonic transducer or vice versa:

$$L = t_{1,2} \cdot c = t_{1,2} \cdot \sqrt{\frac{\kappa RT}{M}} \qquad (2)$$

Regarding the meaning of the individual parameters, reference is made to the explanations given above.

In an embodiment, the nominal value of the distance is stored in an electronic memory of the spirometer or in an electronic memory that is assigned to the spirometer. To give an example, an appropriate electronic memory is a non-volatile memory of the spirometer. To give another example, an appropriate electronic memory is a database in which nominal values of different spirometers are stored together with information referring to which spirometer these nominal values belong. Then, it is only necessary to uniquely identify the spirometer in question to afterwards compare the nominal value of the distance with an actually measured or calculated value of the distance in order to verify the calibration. The unique identification of the spirometers can be done, e.g., by assigning unique numbers or other unique identifiers to the individual spirometers.

All embodiments of the described methods can be combined in any desired way and can be transferred from the method for verifying a calibration of a spirometer to the method for calibrating a spirometer or to the described spirometer, and vice versa. Furthermore, all embodiments and their combinations can be transferred to the described method for verifying a calibration of a spirometer making use of structure-borne noise only.

The invention claimed is:

1. A method for verifying a calibration of an ultrasonic spirometer, the method comprising:
   determining an actual value of a distance between a first ultrasonic transducer and a second ultrasonic transducer of a spirometer;
   determining a difference between the actual value of the distance and a nominal value of the distance that is assigned to the spirometer; and
   (i) accepting an actual calibration of the spirometer if an absolute value of the difference is smaller than or equal to a first threshold value, or
   (ii) refusing an actual calibration of the spirometer if an absolute value of the difference is bigger than the first threshold value,
   wherein the first threshold value is 5% of the nominal value of the distance.

2. The method according to claim 1, wherein determining the actual value of the distance comprises calculating an ultrasonic measurement while there is a non-flowing gas between the first ultrasonic transducer and the second ultrasonic transducer, according to:

$$L = t_{1,2} \cdot c = t_{1,2} \cdot \sqrt{\frac{\kappa RT}{M}}$$

wherein L is the distance between the first ultrasonic transducer and the second ultrasonic transducer, wherein $t_{1,2}$ is a transit time of an ultrasonic pulse calculated from a transit time of an ultrasonic pulse from the first ultrasonic transducer to the second ultrasonic transducer, or a transit time of an ultrasonic pulse calculated from a transit time of an ultrasonic pulse from the second ultrasonic transducer to the first ultrasonic transducer, or a mean transit time calculated from a transit time from the first ultrasonic transducer to the second ultrasonic transducer and a transit time from the second ultrasonic transducer to the first ultrasonic transducer, wherein κ is a ratio $C_P/C_V$ of a specific heat capacity of the gas at constant pressure $C_P$ and a specific heat capacity of the gas at constant volume $C_V$, R is a universal gas constant, T is an absolute temperature of the gas, and M is a molar mass of the gas.

3. The method according to claim 2, wherein the gas is a gas mixture of different gas mixture components, further comprising calculating the molar mass M of the gas mixture according to:

$$M = \sum_{i=1}^{n} f_i \cdot M_i$$

wherein $f_i$ is the fraction of a gas mixture component i in the gas mixture, $M_i$ is the molar mass of the gas mixture component i in the gas mixture, and n is the number of gas mixture components in the gas mixture.

4. The method according to claim 2, wherein the gas is a gas mixture of different gas mixture components, wherein an estimated composition of the gas mixture is used to calculate its molar mass.

5. The method according to claim 4, wherein the gas mixture is ambient air, wherein a molar mass of the ambient air ranges from 25 to 34 g/mol.

6. The method according to claim 2, wherein the absolute temperature of the gas is set to be an absolute temperature of a flow tube holder of the spirometer.

7. The method according to claim 2, wherein the distance is normalized to an arbitrary standard temperature.

8. The method according to claim 1, wherein the verification of calibration takes place when a flow tube is inserted into a flow tube holder of the spirometer.

9. The method according to claim 1, further comprising determining an amount of structure-borne noise of the spirometer, further comprising only accepting the actual calibration of the spirometer if the absolute value of the difference is smaller than or equal to the first threshold value and the amount of structure-borne noise is smaller than or equal to a second threshold value, and further comprising refusing the actual calibration of the spirometer if the absolute value of the difference is smaller than, equal to, or bigger than the first threshold value but the amount of structure-borne noise is bigger than the second threshold value.

10. The method according to claim 9, wherein the second threshold value is 5.0% of a primary received ultrasonic signal, wherein the primary received ultrasonic signal is a signal of a first proper ultrasonic signal detection.

11. The method according to claim 9, wherein the amount of structure-borne noise is determined by measuring an amplitude of the first ultrasonic transducer and/or the second ultrasonic transducer in a time window before a primary received ultrasonic signal is detected, wherein the primary received ultrasonic signal is a signal of a first proper ultrasonic signal detection.

12. The method according to claim 9, wherein the amount of structure-borne noise is determined while there is a non-flowing gas between the first ultrasonic transducer and the second ultrasonic transducer.

13. A spirometer, comprising
a first ultrasonic transducer;
a second ultrasonic transducer; and
a control unit that is specifically adapted and arranged to automatically carry out a method in a predetermined interval or by request of a user, the method comprising:
determining an actual value of a distance between the first ultrasonic transducer and the second ultrasonic transducer;
determining a difference between the actual value of the distance and a nominal value of the distance that is assigned to the spirometer; and
(i) accepting an actual calibration of the spirometer if an absolute value of the difference is smaller than or equal to a first threshold value, or
(ii) refusing an actual calibration of the spirometer if an absolute value of the difference is bigger than the first threshold value,
wherein the first threshold value is 5% of the nominal value of the distance.

14. The spirometer according to claim 13, further comprising an electronic memory, wherein the nominal value of the distance is stored in the electronic memory.

15. The spirometer according to claim 13, wherein determining the actual value of the distance comprises calculating an ultrasonic measurement while there is a non-flowing gas between the first ultrasonic transducer and the second ultrasonic transducer, according to:

$$L = t_{1,2} \cdot c = t_{1,2} \cdot \sqrt{\frac{\kappa RT}{M}}$$

wherein L is the distance between the first ultrasonic transducer and the second ultrasonic transducer, wherein $t_{1,2}$ is a transit time of an ultrasonic pulse calculated from a transit time of an ultrasonic pulse from the first ultrasonic transducer to the second ultrasonic transducer, or a transit time of an ultrasonic pulse calculated from a transit time of an ultrasonic pulse from the second ultrasonic transducer to the first ultrasonic transducer, or a mean transit time calculated from a transit time from the first ultrasonic transducer to the second ultrasonic transducer and a transit time from the second ultrasonic transducer to the first ultrasonic transducer, wherein κ is a ratio $C_P/C_V$ of a specific heat capacity of the gas at constant pressure $C_P$ and a specific heat capacity of the gas at constant volume $C_V$, R is a universal gas constant, T is an absolute temperature of the gas, and M is a molar mass of the gas.

16. The spirometer according to claim 15, wherein the gas is a gas mixture of different gas mixture components, and wherein the method of the control unit further comprises calculating the molar mass M of the gas mixture according to:

$$M = \sum_{i=1}^{n} f_i \cdot M_i$$

wherein $f_i$ is the fraction of a gas mixture component i in the gas mixture, $M_i$ is the molar mass of the gas mixture component i in the gas mixture, and n is the number of gas mixture components in the gas mixture.

17. The spirometer according to claim 13, wherein the control unit is configured to verify a calibration of the spirometer by carrying out the method responsive to an insertion of a flow tube into a flow tube holder of the spirometer.

18. The spirometer according to claim 13, wherein the method of the control unit further comprises determining an amount of structure-borne noise of the spirometer, only accepting the actual calibration of the spirometer if the absolute value of the difference is smaller than or equal to the first threshold value and the amount of structure-borne noise is smaller than or equal to a second threshold value, and refusing the actual calibration of the spirometer if the absolute value of the difference is smaller than, equal to, or bigger than the first threshold value but the amount of structure-borne noise is bigger than the second threshold value, wherein the second threshold value is 5.0% of a primary received ultrasonic signal, wherein the primary received ultrasonic signal is a signal of a first proper ultrasonic signal detection.

19. The spirometer according to claim 18, wherein the method of the control unit further comprising determining the amount of structure-borne noise by measuring an amplitude of the first ultrasonic transducer and/or the second ultrasonic transducer in a time window before the primary received ultrasonic signal is detected.

* * * * *